United States Patent
Buchholz et al.

(12) 
(10) Patent No.: US 6,514,973 B1
(45) Date of Patent: Feb. 4, 2003

(54) COMPOSITIONS FOR THE TREATMENT AND PREVENTION OF NEUROLOGICAL AND PATHOPSYCHOLOGICAL DISEASES

(75) Inventors: Herwig Buchholz, Frankfurt (DE); Jerzy D. Meduski, Playa Del Rey, CA (US)

(73) Assignee: Merck Patent Geseilschaft Mit Beschrankter Haftung, Darmstadt (DE)

( * ) Notice: Subject to any disclaimer, the term of this patent is extended or adjusted under 35 U.S.C. 154(b) by 0 days.

(21) Appl. No.: 09/830,352

(22) PCT Filed: Oct. 13, 1999

(86) PCT No.: PCT/EP99/07688

§ 371 (c)(1), (2), (4) Date: Apr. 25, 2001

(87) PCT Pub. No.: WO00/25793

PCT Pub. Date: May 11, 2000

Related U.S. Application Data

(60) Provisional application No. 60/106,230, filed on Oct. 30, 1998.

(51) Int. Cl.⁷ .................. A61K 31/50; A61K 31/495; A61K 31/205; A61K 31/195
(52) U.S. Cl. .................. 514/249; 514/556; 514/561; 514/562
(58) Field of Search .................. 514/249, 556, 514/561, 562

(56) References Cited

U.S. PATENT DOCUMENTS

| 5,059,595 A | * 10/1991 | Le Grazie |
| 5,538,734 A | * 7/1996 | Le Grazie |
| 5,997,915 A | * 12/1999 | Bailey et al. |

FOREIGN PATENT DOCUMENTS

| DE | 4117629 | 12/1992 |
| WO | 99/37155 | 7/1999 |

OTHER PUBLICATIONS

Duell PB: "Homocyst(e)ine: An important risk factor for atherosclerotic vascular disease" *Current Opinion in Lipidology* vol. 8, No. 1. pp. 28–34, 1997.

* cited by examiner

Primary Examiner—William R. A. Jarvis
(74) Attorney, Agent, or Firm—Millen, White, Zelano & Branigan

(57) ABSTRACT

This invention relates to a composition containing the three active ingredients: a) one or more phosphatidyl serines, b) one or more methyl transporters, and c) one or more compounds selected from methyl and methylene donors.

7 Claims, No Drawings

COMPOSITIONS FOR THE TREATMENT AND PREVENTION OF NEUROLOGICAL AND PATHOPSYCHOLOGICAL DISEASES

This application claims the benefit of priority of U.S. Provisional Application No. 60/106,230, filed Oct. 30, 1998.

The invention relates to compositions for the treatment and prevention of transmethylation disorders, preferably neurological and pathopsychological diseases.

It has been documented that neurological symptoms are associated with abnormally high levels of homocysteine in the blood (hyperhomocysteinemia or homocysteinuria). Investigations indicate that hyperhomocysteinemia contributes to microcephaly, mental retardation severe psychomotor retardation, convulsions, apneic spells, and even death. In several patients with methylenetetrahydrofolate reductase deficiency, which is one of the reasons for homocysteine accumulation, demyelination of the brain and subacute combined degeneration of the spinal cord was reported. Results of several studies have also shown that defective methylenetetrahydrofolate reductase and elevated homocysteine level are risk factors for neural tube defects such as spina bifida and anencephaly. Furthermore, elevated homocysteine levels have been found in amniotic fluid of pregnant women having fetuses with neural tube defects. The existence of a linear connection between the homocysteine level of mother and fetus has been reported.

In the human body, homocysteine is formed from methionine. In a simplified description methionine is condensed with adenosine triphosphate to produce S-adenosylmethionine and the latter is converted to S-adenosylhomocysteine. S-Adenosylhomocysteine is rapidly metabolised to homocysteine which is an important branch-point metabolite. It can be regenerated back to methionine, it can be converted to S-adenosylhomocysteine or it can enter the trans-sulfuration-pathway by reaction to cystathionine.

In the past, it has been the aim of several studies to treat hyperhomocysteinemia, i.e. to lower the elevated homocysteine levels. It is known that betaine and choline, which is converted to betaine by oxidation, may act as methylating agents. For example, the enzyme-catalyzed reaction between betaine and homocysteine in the human organism leads to the formation of methionine and dimethylglycine and the treatment with betaine is known to be efficient in lowering homocysteine concentrations. Other attempts included the supplementation of vitamins like vitamin $B_6$, vitamin $B_{12}$ or usual multivitamins, vitamin $B_6$ in combination with a methionine restriction, methylcobalamine, folic acid, folic acid together with vitamins $B_6$ and $B_{12}$, folate, and occasionally folate in combination with vitamin $B_6$, vitamin $B_{12}$, choline or betaine (M. R. Malinow, J. Nutr. 126 (1996) 1238–1243).

However, the effectiveness of the previously applied compositions was not satisfactory. The treatment approach has not been linked to the complexity of the transmethylation metabolism.

The invention had the object of providing new compositions for the treatment and prevention of transmethylation disorders, preferably neurological and pathopsychological diseases, which improve the treatment significantly.

It has now been found that this object can be achieved with compositions which comprise one or more active ingredients and, optionally, one or more natural substances, solid, liquid and/or semiliquid excipients or auxiliaries, characterized in that the active ingredients consist of a) a component A consisting of one or more phosphatidylserines, b) a component B consisting of one or more methyl transporters, and c) a component C consisting of one or more compounds selected from methyl and methylene donors, provided that phosphatidylserines and compounds with methyl transporting properties do not form part of component C.

The new compositions according to the invention also affect the whole area of cardiovascular dysfunctions.

The invention furthermore relates to compositions for the treatment and prevention of diseases associated with hyperhomocysteinemia.

Phosphatidylserines, which are donors of one carbon groups, are naturally occurring phospholipid components of cellular membranes. These biomembranes are involved in a number of vital processes, such as nerve cell differentiation, activation and renewal, nerve transmitter production, ion transport etc. Phosphatidyiserines are found in all cells and organs of the body, but they are most concentrated in nerve cells of the brain and are essential for several brain functions, e.g. for the conduction of nerve impulses and the production, storage and release of neurotransmitters.

It has been documented that the oral supplementation with 200 to 300 mg of phosphatidylserines per day for 2 to 6 months improves brain metabolism and benefits cognitive functions such as memory, thinking, learning, and the ability to concentrate especially in aging people and in patients with certain neurological and pathopsychological conditions. The effectiveness of phosphatidylserines in the treatment of senile dementia, Parkinson's disease epilepsy, depression, and age-associated memory impairment has also been demonstrated in several studies.

Posphatidylserines appear to make pro-homeostatic contributions and provide metabolic support to a wide range of brain functions. It has been assumed that phosphatidylserines are able to stimulate glucose metabolism in the brain and also increase the number of neurotransmitter receptor sites.

Phosphatidylserines are not abundant in common foods, but they have a good availability by oral route and are suitable as dietary supplement. They appear in the blood at about 30 minutes after oral administration and are able to cross the blood-brain barrier. Phosphatidylserines reach the brain within minutes after being absorbed.

As mentioned above, it has been documented that many neurological symptoms are associated with hyperhomocysteinemia. According to the invention it has now been found that an elevated homocysteine level is a sign of the inadequate methyl pool involving both methyl donors and methyl transporters. Therefore, the homocysteine level in the human body may be used as an indicator of the state of the transmethylation metabolism in certain cases.

In the human body, one-carbon or $C_1$ groups exist in several oxidation states. These groups include methyl groups, methylene groups, methylidyne groups, carbonyl groups, formyl groups, hydroxymethyl groups, and carboxyl groups. Practically, these groups can be divided into groups at the oxidation level of methanol, formaldehyde, and formate Exemplary sources of the methyl group (methanol oxidation level) are methionine, adenosylmethionine, methylated glycines, and choline. The sources of methylene group (formaldehyde oxidation level) are serine and glycine. One of the sources of the group at the formate oxidation level is e.g. histidine. All of these one-carbon groups form the so-called one-carbon pool and participate in many important reactions. As the methyl group is biochemically the most ubiquitous, the one-carbon pool is often referred to as the methyl pool.

The metabolic events of methyl groups are usually specified as transmethylation, whereas the involved molecules are called transmethylators. Depending upon their function during the metabolic events, the transmethylators are classified as methyl donors, methyl transporters, and methyl acceptors. Methyl donors are e.g. methionine, S-adenosylmethionine, choline, methylglycine (sarcosine), dimethylglycine, and trimethylglycine (betaine). Methyl transporters are e.g. tetrahydrofolates which are derived from folic acid and methylcobalamine and adenosylcobalamine, which are coenzymes derived from vitamin $B_{12}$. Methyl acceptors include all nucleic acids, proteins, most of them enzyme proteins, phospholipids (components of biomembranes), and many biological amines, which serve as neurotransmitters in many cases.

The properly functioning methylation of these four classes of acceptor molecules is of importance for their biochemical activity. The methylation of the nucleic acids assures their structure stability and their accurate genetic performance. The methylation of the enzyme proteins ensures their specificity and efficiency and prevents the accumulation of intermediary metabolites. The methylation of the phospholipids provides an optimal cytomembrane functionality and the methylation of the biological amines guarantees their specificity and effectiveness.

A decrease of the pool of methyl donors and/or of methyl transporters may lead to transmethylation disorders. Impairments of the methylation (also referred to as demethylations) of one or more components of the four methyl acceptor classes may occur and dysfunctions of these methyl acceptors may be the consequence. Metabolic dysfunctions and diseases may result.

Major neurological and pathopsychological diseases associated with hyperhomocysteinemia are depression, premature old age or senilism, dementia, Pick's disease, metabolic myelopathy, peripheral neuropathy, neural tube defects, e.g. anencephaly, spina bifida or encephalocoele, gait disturbances, and muscle weakness. The invention furthermore relates to compositions for treatment and prevention of these diseases.

The expression "methyl donor" (component C) stands for substances which are able to deliver methyl groups to transporter molecules. Important methyl donors are e.g. choline and S-adenosylmethionine.

Choline is required for the biosynthesis of essential membrane phospholipids. It is a precursor for the biosynthesis of the neurotransmitter acetylcholine and also is an important source of labile methyl groups. Since the late 1970's the relation between choline levels and the synthesis of acetylcholine was extensively studied. It was found that the administration of choline caused significant sequential elevations in serum choline, brain choline, and brain acetylcholine levels. Recently, much attention has been paid to the effect of supplemental choline upon brain function, i.e. upon the enhancement of acetylcholine synthesis and release. Choline supplementation has been advocated as a means to prevent the decline in acetylcholine production and to enhance cholinergic transmission.

Choline was used as a therapeutic agent for suppression of the major side-effects of antipsychotic drugs such as tardive dyskenesia and for treatment of several other diseases that are thought to involve cholinergic neurons. These disorders include both brain diseases such as mania and memory loss and peripheral diseases such as myastenic syndromes.

S-Adenosylmethionine serves as a precursor in the biosynthesis of polyamines. It is synthesized from adenosyltriphosphate and L-methionine by methionine-adenosyltransferase. Recently, the effect of oral S-adenosylmethionine in doses of 400 mg on plasma levels of several methionine metabolites such as the demethylated product S-adenosylhomocysteine, homocysteine, and methionine was investigated. It is known that disorders of homocysteine metabolism contribute to cerebral, peripheral and coronary vascular disease. Administration of S-adenosylmethionine produces significant improvements in patients with depressive syndromes.

The expression "methylene donor" (component C) stands for substances which are able to deliver methylene groups to transporter molecules. A known methylene donor is e.g. serine, a component of the phosphatidylserines.

The expression "methyl transporter" (component B) is used for substances which are able to transfer methyl groups to acceptor molecules. Therefore, the methyl transporters have to contain a transferable methyl group or they have to be able to remove a transferable methyl group from the donor molecules. Alternatively, they have to be able to remove another group from the donor molecules, but a group that may be converted to a transferable methyl group during the metabolic events or they have to contain such a group. For example, it is known that tetrahydrofolate may be converted to the 5-methyl derivative, which is able to transfer its methyl group to acceptor molecules. Furthermore, it is documented that the 5-methyl, 5-formyl, 10-formyl, 5,10-methylene, and 5,10-methenyl derivatives of tetrahydrofolate may be converted enzymatically into each other, i.e. each of these compounds may be converted to the 5-methyl derivative. Therefore, all of the abovementioned derivatives of tetrahydrofolate are methyl transporters within the meaning of the present invention.

If component C of the inventive compositions consists only of methylene donors, component B has to comprise at least one methyl transporter which is able to remove methylene groups from the methylene donors and convert these methylene groups to transferable methyl groups.

On principle, all known phosphatidylserines—their physiologically acceptable salts included—may be used as constituents of component A of the inventive compositions. The phosphatidylserines may contain saturated and/or unsaturated fatty acid groups, e.g. groups selected from palmitic acid, stearic acid, oleic acid, linoleic acid, and linolenic acid groups.

Preferred methyl transporters (component B) are selected from dihydrofolic acid, tetrahydrofolic acid, 5-methyltetrahydrofolic acid, 5-formyltetrahydrofolic acid, 10-formyltetrahydrofolic acid, 5,10-methylenetetrahydrofolic acid, 5,10-methenyltetrahydrofolic acid or their physiologically acceptable salts. Particularly preferred methyl transporters are derivatives of L- or (S)-glutamic acid and are selected from (6S)-tetrahydrofolic acid, 5-methyl-(6S)-tetrahydrofolic acid, 5-formyl-(6S)-tetrahydrofolic acid, 10-formyl-(6R)-tetrahydrofolic acid, 5,10-methylene-(6R)-tetrahydrofolic acid, 5,10-methenyl-(6R)-tetrahydrofolic acid or their physiologically acceptable salts. Among these the methyl transporter 5-methyl-(6S)-tetrahydrofolic acid (which is also referred to as L-5-methyltetrahydrofolic acid) or a physiologically acceptable salt thereof is especially preferred. L-5-methyltetrahydrofolic acid penetrates all organs of the human body.

Preferred methyl or methylene donors (component C) are selected from betaine, dimethylglycine, sarcosine, methionine, S-adenosylmethionine, choline, serine, and their physiologically acceptable salts.

The physiologically acceptable salts of the phosphatidylserines, methyl donors and methylene donors can be obtained by converting a base of these compounds with an acid into the associated acid addition salt. Acids which yield physiologically harmless salts are e.g. inorganic acids, for example sulfuric acid, nitric acid, hydrochloric acid, phosphoric acids, such as orthophosphoric acid, organic acids, in particular aliphatic, alicyclic, araliphatic, aromatic or heterocyclic monobasic or polybasic carboxylic or sulfuric acids, for example formic acid, acetic acid, propionic acid, pivalic acid, diethylacetic acid, malonic acid, succinic acid, fumaric acid, maleic acid, lactic acid, tartaric acid, malic acid, citric acid, gluconic acid, ascorbic acid or nicotinic acid.

Furthermore, the physiologically acceptable salts of the phosphatidylserines, methyl donors and methylene donors can be obtained by converting an acid of these compounds with a base into one of its physiologically harmless metal salts or ammonium salts. Suitable salts in this context are, in particular, the sodium, potassium, magnesium, calcium and ammonium salts, and also substituted ammonium salts, for example the dimethyl-, diethyl- or diisopropylammonium salts, monoethanol-, diethanol- or diisopropylammonium salts, cyclohexyl- or dicyclohexylammonium salts or dibenzylethylenediammonium salts, and also, for example, salts with arginine or lysine.

The physiologically acceptable salts of the methyl transporters are selected from alkali metal or alkaline earth metal salts, preferably from sodium, potassium, magnesium, and calcium salts.

If amino acids mentioned above or below may occur in more than one enantiomeric form, all of these forms and also mixtures thereof are included (e.g. the DL-forms). Preferably, the amino acids mentioned have (S)- or (L)-configuration even if this is not stated explicitly.

In preferred compositions according to the invention the molar ratio of component A: component B: component C is from 500:1:30,000 to 1:1:300.

The present invention relates to compositions containing or comprising one or more active ingredients according to claim 1.

For instance, the present invention relates to food or food supplement compositions comprising one or more active ingredients according to claim 1. These food or food supplement compositions may optionally also comprise one or more solid, liquid and/or semiliquid excipients or auxiliaries which are known from prior art. The inventive food compositions comprise one or more active ingredients and one or more nutritional substances. The inventive food supplement compositions do not need to contain nutritional substances, but can be used for the preparation of food compositions.

The nutritional substances encompass all materials which are suited for consumption both by animals and/or by human beings, e.g. vitamins and provitamins thereof, fats, minerals or amino acids. Nutritional substances, which can be part of the inventive food compositions are e.g. materials, which are derived substantially from a single natural source such as sugar, unsweetened juice, nectar or puree from a single species of plant, such as unsweetened apple juice (including a blend of different varieties of apple juice), grapefruit juice, orange juice, apple sauce, apricot nectar, tomato juice, tomato sauce, tomato puree, grain plants of a single species and materials produced from grain plants of a single species, such as corn syrup, rye flour, wheat flour or oat bran. The inventive food compositions also comprise nutritional substances which are mixtures of different of the abovementioned materials, such as multivitamin preparations or sweetened juice. Further nutritional substances, which can be part of the inventive food compositions are e.g. food preparations such as breakfast foods, e.g. prepared cereals, toaster pastries, and breakfast drink mixes, infant formulas, dietary supplements, complete diet formulas, and weight-loss preparations, such as weight-loss drinks and weight-loss bars. Further examples of nutritional substances, which can be part of the inventive food compositions are e.g. animal feed or animal feed supplements (for example for poultry), and pet foods.

The nutritional substances include all edible combinations of carbohydrates, lipids, proteins, inorganic elements, trace elements, vitamins, water, and active metabolites of plants and animals.

The inventive food or food supplement compositions are preferably used for oral administration, e.g. in the form of food, pills, tablets, capsules, powders, syrups, solutions, or suspensions or as products absorbable through mucosal membranes.

The inventive food or food supplement compositions can be prepared by methods which are well-known to the expert.

Furthermore, the present invention relates to pharmaceutical compositions comprising one or more active ingredients according to claim 1. These inventive pharmaceutical compositions can be used in human or veterinary medicine. Suitable excipients are organic or inorganic substances which are suitable for enteral, parenteral or topical administration and which do not react with the novel compounds, for example water, vegetable oils, benzyl alcohols, alkylene glycols, polyethylene glycols, glycerol triacetate, gelatin, carbohydrates such as lactose or starch, magnesium stearate, talc, petrolatum. Used for oral administration are, in particular, tablets, pills, coated tablets, capsules, powders, granules, syrups, solutions or drops, for rectal administration are suppositories, for parenteral administration are solutions, preferably oily or aqueous solutions, also suspensions, emulsions or implants, for topical administration are ointments, creams or powders. The novel pharmaceutical compositions can also be lyophilized, and the resulting lyophilizates be used, for example, for producing injection preparations. The stated preparations can be sterilized andlor comprise auxiliaries such as lubricants, preservatives, stabilizers and/or wetting agents, emulsifiers, salts to influence the osmotic pressure, buffer substances, colorants, flavourings and/or several other active substances, for example one or more vitamins.

The specific dose for each patient depends on a wide variety of factors, for example on the activity of the specific compounds employed, on the age, bodyweight, general state of health, sex, on the diet, the time and route of administration, on the rate of excretion, medicinal substance combination and severity of the particular disorder for which the therapy is applied. Oral administration is preferred.

The invention furthermore relates to the use of one or more compounds selected from phosphatidyl serines, one or more compounds selected from methyl transporters, and one or more compounds selected from methyl and methylene donors for the preparation of compositions (e.g. pharmaceutical, food or food supplement compositions) for the treatment of transmethylation disorders in particular by non-chemical means. The phosphatidyl serines and the compounds with methyl transporting properties do not form part of the the group of methyl and methylene donors. The phosphatidylserines, methyl transporters, methyl donors, and methylene donors can for this purpose be converted into a suitable dosage form, optionally together with one or more nutritional substances, solid, liquid and/or semiliquid excipients or auxiliaries and, where appropriate, in combination with one or more other active substances.

The inventive compositions can be used for controlling transmethylation disorders, in particular neurological and pathopsychological diseases.

The compounds used in the inventive compositions are commercially available or may be prepared in accordance with methods known per se and as described in the literature (for example in the standard works such as Houben-Weyl, Methoden der organischen Chemie [Methods of Organic Chemistry], Georg-Thieme-Verlag, Stuttgart).

From the foregoing description, one skilled in the art can easily ascertain the essential characteristics of this invention and, without departing from the spirit and scope thereof, can make various changes and modifications of the invention to adapt it to various usages and conditions. Therefore, the following examples should be interpreted as an illustration of the present invention but not as a limitation thereof.

The following example 1 relates to the composition of active ingredients for one single serving.

EXAMPLE 1

The active ingredients of the inventive composition consist of

| | |
|---|---|
| Phosphatidylserine | 50 mg |
| L-5-Methyltetrahydrofolic acid, calcium salt | 0.5 mg |
| Choline | 100 mg |
| S-Adenosylmethionine | 200 mg |
| Serine | 200 mg | and are related to an average bodyweight of about 70 kg.

The following example A relates to a pharmaceutical preparation:

Example A

Tablets

A mixture of 1 kg of the composition of active ingredients as given in example 1 and the appropriate amounts of excipients (4 kg of lactose, 1.2 kg of potato starch, 0.2 kg of talc, and 0.1 kg of magnesium stearate) is compressed to tablets in a customary way so that each tablet comprises 500 mg of the composition of active ingredients as given in example 1.

What is claimed is:

1. A composition comprising active ingredients and, optionally, one or more nutritional substances, solid, liquid and/or semiliquid excipients or auxiliaries, wherein the active ingredients comprise:

a) a component A comprising one or more phosphatidyl serines, b) a component B comprising one or more methyl transporters, and c) a component C comprising one or more compounds selected from methyl and methylene donors, provided that phosphatidyl serines and compounds with methyl transporting properties do not form part of component C.

2. A composition according to claim 1, wherein component B comprises one or more compounds selected from dihydrofolic acid, tetrahydrofolic acid, 5-methyltetrahydrofolic acid, 5-formyltetrahydrofolic acid, 10-formyltetrahydrofolic acid, 5,10-methylenetetrahydrofolic acid, 5,10-methenyltetrahydrofolic acid or their physiologically acceptable salts.

3. A composition according to claim 2, wherein component B comprises L-5-methyltetrahydrofolic acid or a physiologically acceptable salt thereof.

4. A composition according to claim 1, wherein component C comprises one or more compounds selected from betaine, dimethylglycine, sarcosine, methionine, S-adenosyl-methionine, choline, and serine or their physiologically acceptable salts.

5. A process for preparing a composition for the treatment of transmethylation disorders comprising bringing one or more compounds selected from phosphatidyl serines, one or more compounds selected from methyl transporters, and one or more compounds selected from methyl and methylene donors according to claim 1 and/or the physiologically acceptable salt thereof, into a suitable pharmaceutical form together with at least one solid, liquid or semi-liquid excipient or auxiliary.

6. A composition according to claim 1, wherein the molar ratio of component A: component B; and component C is from 500:1:30,000 to 1:1 300.

7. A food supplement comprising the composition according to claim 1.

* * * * *